(12) United States Patent
Charvet et al.

(10) Patent No.: US 9,018,190 B2
(45) Date of Patent: *Apr. 28, 2015

(54) FUNCTIONALIZED OLIGOSACCHARIDES

(75) Inventors: Richard Charvet, Rillieux la Pape (FR); Remi Soula, Lyons (FR); Olivier Soula, Meyzieu (FR)

(73) Assignee: ADOCIA, Lyons (FR)

(*) Notice: Subject to any disclaimer, the term of this patent is extended or adjusted under 35 U.S.C. 154(b) by 117 days.

This patent is subject to a terminal disclaimer.

(21) Appl. No.: 13/468,849

(22) Filed: May 10, 2012

(65) Prior Publication Data

US 2012/0309680 A1    Dec. 6, 2012

Related U.S. Application Data

(63) Continuation-in-part of application No. 13/287,793, filed on Nov. 2, 2011, now abandoned.

(60) Provisional application No. 61/541,606, filed on Sep. 30, 2011, provisional application No. 61/484,461, filed on May 10, 2011.

(30) Foreign Application Priority Data

May 10, 2011 (FR) .................... 11 54039
Sep. 30, 2011 (FR) .................... 11 58885

(51) Int. Cl.
*A61K 31/721* (2006.01)
*A61K 47/36* (2006.01)
*C08B 37/02* (2006.01)
*A61K 38/28* (2006.01)
*A61K 9/00* (2006.01)
*A61K 47/48* (2006.01)

(52) U.S. Cl.
CPC .............. *A61K 38/28* (2013.01); *A61K 9/0019* (2013.01); *A61K 47/4823* (2013.01); *C08B 37/0021* (2013.01)

(58) Field of Classification Search
None
See application file for complete search history.

(56) References Cited

U.S. PATENT DOCUMENTS

| | | | |
|---|---|---|---|
| 2,847,385 | A | 8/1958 | Hiler |
| 4,006,059 | A | 2/1977 | Butler |
| 4,472,385 | A | 9/1984 | Brange et al. |
| 4,826,818 | A | 5/1989 | Mori et al. |
| 5,929,027 | A | 7/1999 | Takama et al. |
| 8,241,620 | B2 | 8/2012 | Dahri-Correia et al. |
| 2004/0131583 | A1 | 7/2004 | Barritault et al. |
| 2004/0234616 | A1 | 11/2004 | Sabetsky |
| 2007/0191757 | A1 | 8/2007 | Steiner et al. |
| 2007/0235365 | A1 | 10/2007 | Pohl et al. |
| 2008/0014250 | A1 | 1/2008 | Soula et al. |
| 2008/0039365 | A1 | 2/2008 | Steiner et al. |
| 2008/0039368 | A1 | 2/2008 | Steiner et al. |
| 2008/0096800 | A1 | 4/2008 | Pohl et al. |
| 2008/0234227 | A1 | 9/2008 | Soula et al. |
| 2009/0221805 | A1 | 9/2009 | Dahri-Correia et al. |
| 2009/0291114 | A1 | 11/2009 | Soula et al. |
| 2010/0166867 | A1 | 7/2010 | Soula et al. |
| 2010/0167991 | A1 | 7/2010 | Soula et al. |
| 2010/0227795 | A1 | 9/2010 | Steiner et al. |
| 2010/0249020 | A1 | 9/2010 | Soula et al. |
| 2011/0159068 | A1 | 6/2011 | Soula et al. |
| 2011/0212901 | A1 | 9/2011 | Akiyoshi et al. |
| 2012/0041079 | A1 | 2/2012 | Soula et al. |
| 2012/0094902 | A1 | 4/2012 | Soula et al. |
| 2012/0295833 | A1 | 11/2012 | Charvet |
| 2012/0309680 | A1 | 12/2012 | Charvet |

FOREIGN PATENT DOCUMENTS

| | | |
|---|---|---|
| EP | 0 214 826 A2 | 3/1987 |
| EP | 0 441 563 A2 | 8/1991 |
| EP | 0 648 495 A2 | 4/1995 |
| EP | 0 681 833 A2 | 11/1995 |
| EP | 0 700 683 A1 | 3/1996 |
| EP | 1 623 979 A1 | 2/2006 |
| FR | 2 224 164 | 10/1974 |
| FR | 2 914 305 A1 | 10/2008 |
| FR | 2 936 800 A1 | 4/2010 |
| WO | WO 88/06599 A1 | 9/1988 |
| WO | WO 91/09617 A1 | 7/1991 |
| WO | WO 97/49386 A1 | 12/1997 |
| WO | WO 99/34821 A1 | 7/1999 |
| WO | WO 02/053190 A2 | 7/2002 |
| WO | WO 03/000202 A2 | 1/2003 |

(Continued)

OTHER PUBLICATIONS

Heinze et al, Functional Polymers Based on Dextran, Adv Polym Sci, 2006, 205, pp. 199-291.*
Jul. 24, 2013 Office Action issued in U.S. Appl. No. 12/662,036.
R. Janowski, et al., "Two Polymorphs of a Covalent Complex Between Papain and a Diazomethylketone Inhibitor," J. Peptide Res. 64, 2004, pp. 141-150.
Demitras et al, Inorganic Chemistry, Prentice-Hall International Inc., 1972, enclosed pp. 1-5.
Engelmann et al., "Preparation of Starch Carbamates in Homogeneous Phase using Different Mixing Conditions," *Starch/Stärke*, 2001, pp. 560-569, vol. 53, Wiley-VCH Verlag GmbH.
Larsen, "Dextran prodrugs—structure and stability in relation to therapeutic activity," *Advanced Drug Delivery Reviews*, 1989, pp. 103-154, vol. 3, Elsevier.

(Continued)

*Primary Examiner* — Julie Ha
*Assistant Examiner* — Li Ni Komatsu
(74) *Attorney, Agent, or Firm* — Oliff PLC

(57) ABSTRACT

The invention relates to an oligodextran, chosen from dextrans whose average degree of polymerization is less than 10, modified by at least one substituent of general formula I:

—$R_1$-[[AA]-[$R_2$]$_n$]$_m$    formula I

It also relates to a pharmaceutical composition characterized in that it comprises an oligosaccharide according to the invention and an active ingredient is chosen from the group consisting of proteins, glycoproteins, peptides and non-peptide therapeutic molecules.

4 Claims, No Drawings

(56) References Cited

FOREIGN PATENT DOCUMENTS

| WO | WO 2004/093833 A2 | 11/2004 |
|---|---|---|
| WO | WO 2005/072803 A1 | 8/2005 |
| WO | WO 2005/089722 A1 | 9/2005 |
| WO | WO 2007/038773 A1 | 4/2007 |
| WO | WO 2007/041481 A1 | 4/2007 |
| WO | WO 2007/116143 A1 | 10/2007 |
| WO | WO 2007/121256 A2 | 10/2007 |
| WO | WO 2008/038111 A1 | 4/2008 |
| WO | WO 2008/084237 A2 | 7/2008 |
| WO | WO 2008/124522 A2 | 10/2008 |
| WO | WO 2008/152106 A1 | 12/2008 |
| WO | WO 2009/048945 A1 | 4/2009 |
| WO | WO 2009/048959 A1 | 4/2009 |
| WO | WO 2009/127940 A1 | 10/2009 |
| WO | WO 2010/028055 A1 | 3/2010 |
| WO | WO 2010/041138 A2 | 4/2010 |
| WO | WO 2010/053140 A1 | 5/2010 |
| WO | WO 2010/058106 A1 | 5/2010 |
| WO | WO 2010/102020 A1 | 9/2010 |
| WO | WO 2010/122385 A1 | 10/2010 |
| WO | WO 2010/149772 A1 | 12/2010 |
| WO | WO 2011/098962 A2 | 8/2011 |

OTHER PUBLICATIONS

Lou, Xianwen et al., "Simulation of size exclusion chromatography for characterization of supramolecular complex: a theoretical study," *Journal of Chromatography A*, 2004, vol. 1029, pp. 67-75.

Ouari et al., "Synthesis of a Glycolipidic Amphiphilic Nitrone as a New Spin Trap," J. Org. Chem., 1999, pp. 3554-3556, vol. 64, American Chemical Society (with 10 pages of supporting information).

Shen et al., "Synthesis and Characterization of Cellulose Carbamates Having α-Amino Acid Moieties," *Polymer Bulletin*, 2005, pp. 317-322, vol. 55.

Tschantz, William R. et al., "Substrate Binding Is Required for Release of Product from Mammalian Protein Farnesyltransferase," *The Journal of Biological Chemistry*, 1997, vol. 272, No. 15, pp. 9989-9993.

Won, "Synthesis of heterobifunctional poly(ethylene glycol) containing an acryloyl group at one end and an isocyanate group at the other end," *Polymer Bulletin*, 2004, pp. 109-115, vol. 52.

Definition of Phenylalanine, from Croatian English Chemistry Dictionary & Glossary (http://glossary.periodni.com/glossary.php?en=phenylalanine, enclosed, pp. 1-2, Accessed Jan. 17, 2013.

Aug. 7, 2012 Written Opinion of the International Searching Authority issued in International Application No. PCT/IB2010/000711.

Sep. 19, 2012 Office Action issued in U.S. Appl. No. 12/662,036.
Feb. 22, 2013 Office Action issued in U.S. Appl. No. 12/662,036.
Feb. 28, 2013 Office Action issued in U.S. Appl. No. 13/468,799.
U.S. Appl. No. 12/662,036 to Soula et al., filed Mar. 29, 2010.
U.S. Appl. No. 13/287,793 to Soula et al., filed Nov. 2, 2011.
U.S. Appl. No. 13/468,799 to Charvet et al., May 10, 2012.
U.S. Appl. No. 13/668,000 to Soula et al., filed Nov. 2, 2012.

Baudys et al., "Extending Insulin Action in Vivo by Conjugation to Carboxymethyl Dextran," *Bioconjugate Chem.*, vol. 9, pp. 176-183, 1998.

Brange et al., "Insulin analogs with improved pharmacokinetic profiles," *Advanced Drug Delivery Reviews*, vol. 35, pp. 307-335, 1999.

Carpino et al., "Efficiency in Peptide Coupling: 1-Hydroxy-7-azabenzotriazole vs 3,4-Dihydro-3-hydroxy-4-oxo-1,2,3-benzotriazine," *Journal of Organic Chemistry*, vol. 60, pp. 3561-3564, 1995.

Caulfield et al., "The Permeability of Glomerular Capillaries to Graded Dextrans," *The Journal of Cell Biology*, vol. 63, pp. 883-903, 1974.

Chang et al., "Permselectivity of the glomerular capillary wall: III. Restricted transport of polyanions," *Kidney International*, vol. 8, pp. 212-218, 1975.

Arranz et al., "Water-insoluble dextrans by grafting, $3_{a)}$ Reaction of dextran with butyl isocyanate. Chemical hydrolysis," *Makromol. Chem.*, vol. 188, pp. 2831-2838, 1987.

Giger et al., "Suppression of Insulin Aggregation by Heparin," *Biomacromolecules*, vol. 9, pp. 2338-2344, 2008.

Tsai et al., "Synthesis of Amino Acid Ester Isocyanates: Methyl (S)-2-Isocyanato-3-Phenylpropanoate [Benzenepropanoic acid, α-isocyanato-, methyl ester, (S)]," *Organic Syntheses Coll.*, vol. 10, p. 544, 2004; vol. 78, p. 220, 2002.

Oct. 14, 2009 French Search Report issued in French Patent Application No. 0901478 (with translation).

Dec. 12, 2011 French Search Report issued in French Patent Application No. 1154039 (with translation).

May 3, 2012 French Search Report issued in French Patent Application No. 1158885 (with translation).

Jul. 12, 2010 International Search Report issued in International Patent Application No. PCT/IB2010/000711 (with translation).

Apr. 2, 2013 International Search Report issued in PCR/FR2012/052543.

"Polymer Molecular Weight Distribution and Definitions of MW Averages;" Jun. 10, 2011; pp. 1-4; www.agilent.com/chem.

"Definition of derivative and analog;" accessed Jul. 7, 2005; pp. 1-5; http://cancerweb.ncl.ac.uk/omd/about.html.

U.S. Office Action dated Jun. 25, 2014 from U.S. Appl. No. 13/668,000.

\* cited by examiner

FUNCTIONALIZED OLIGOSACCHARIDES

This Application is a Continuation-in-Part of U.S. application Ser. No. 13/287,793 filed Nov. 2, 2011. This Application is also a Non-Provisional of U.S. Provisional Applications Nos. 61/541,606 and 61/484,461 filed Sep. 30, 2011 and May 10, 2011, respectively. The disclosure of the prior applications is hereby incorporated by reference herein in its entirety.

BACKGROUND

The present invention relates to anionic oligosaccharides intended for therapeutic and/or prophylactic use, for the administration of active ingredient(s) to humans or to animals.

The oligosaccharides according to the invention containing carboxyl groups have, because of their structure and their biocompatibility, some value for the pharmaceutical industry, especially for the stabilization of active ingredients, for example of protein active ingredients.

Surprisingly and despite the reduction of the length of the macromolecular chain, the oligosaccharides according to the invention preserve the property of creating interactions with active ingredients, for example protein active ingredients.

Moreover, the functionalization of these oligosaccharides by carboxyl groups advantageously makes it possible to modulate the forces of interaction brought into play between the oligosaccharide and the active ingredient.

The aim of the present invention is to provide oligosaccharides intended for the stabilization, administration and delivery of active ingredients which can be prepared by methods that are relatively simple to carry out. The aim of the present invention is thus to provide oligosaccharides capable of allowing the stabilization, administration and delivery of a wide range of active ingredients.

The aim of the present invention is also to obtain oligosaccharides with a degree of functionalization with anionic groups which may be higher than two carboxylate groups per saccharide unit.

The aim of the invention is also the production of oligosaccharides which may exhibit a biodegradability that is sufficiently rapid and appropriate for their use in the preparation of a large category of pharmaceutical formulations, including for medicaments intended for chronic administration and/or with a high frequency. In addition to the requirement for a modulable biodegradability after administration, the aim of the invention is to provide oligosaccharides which meet the constraints established by the pharmaceutical industry, especially in terms of stability under normal preservation and storage conditions and especially in solution.

SUMMARY

The present invention relates to an oligodextran, chosen from dextrans whose average degree of polymerization is less than 10, modified by:
at least one substituent of general formula I:

formula I the substituents being identical or different when there are at least two substituents, in which:
the radical -[AA]- denotes an amino acid residue attached to the dextran backbone by means of a linker arm —$R_1$—, and optionally bearing a radical —$[R_2]_n$
the linker arm —$R_1$— is a C1 to C15 carbon chain optionally substituted and/or containing at least one heteroatom (such as O, N and S) and optionally a carboxylic acid functional group; it forms with the amino acid residue [AA] an amide bond and is directly attached to the dextran backbone by an ester, carbamate or ether type bond
the radical —$R_2$ is an optionally substituted C1 to C18 carbon chain,
n being 0, 1 or 2,
m being 1 or 2,
the degree of substitution j, with —R1-[[AA]-[R2]n]m when m>0 being between 0.01 and 2.9, and,
optionally,
one or more substituents of the same general formula I, in which m=0
—$R_1$ is a C1 to C15 carbon chain, optionally substituted and/or containing at least one heteroatom (such as O, N and S) and at least one carboxylic acid functional group
the degree of substitution i, with —$R_1$ being between 0.1 and 3,
and,
when m or n is equal to 0, then the free salifiable functional groups are in the form of salts of alkali metal cations,
i+j≤3.

DETAILED DESCRIPTION

In one embodiment, the oligodextran is chosen from dextrans modified by:
at least one substituent of general formula I:

formula I the substituents being identical or different when there are at least two substituents, in which:
the radical -[AA]- denotes an amino acid residue attached to the dextran backbone by means of a linker arm —$R_1$—, and optionally bearing a radical —$[R_2]_n$
the linker arm —$R_1$— is a C1 to C15 carbon chain optionally substituted and/or containing at least one heteroatom (such as O, N and S) and optionally a carboxylic acid functional group; it forms with the amino acid residue [AA] an amide bond and is directly attached to the dextran backbone by an ester, carbamate or ether type bond
the radical —$R_2$ is an optionally substituted C1 to C18 carbon chain,
n being 0, 1 or 2,
m being 1 or 2,
the degree of substitution j, with —R1-[[AA]-[R2]n]m when m>0 being between 0.01 and 2.9, and,
optionally,
one or more substituents —R'1- which is a C1 to C15 carbon chain, optionally substituted and/or containing at least one heteroatom (such as O, N and S) and at least one acid functional group in the form of a salt of alkali metal cations and is directly attached to the dextran backbone by an ester, carbamate or ether type bond
the degree of substitution i, with —R'1-, being between 0.1 and 3, and
—R'1- identical or different from —R1-,
and,
when n is equal to 0, then the free salifiable functional groups are in the form of salts of alkali metal cations, and
i+j≤3.

The term heteroatoms is understood to mean an oxygen, nitrogen or sulphur atom.

In one embodiment, the linker arm —R1- forms with the amino acid residue [AA] an amide bond and is directly attached to the dextran backbone by an ether bond.

In one embodiment, the linker arm —R1- forms with the amino acid residue [AA] an amide bond and is directly attached to the dextran backbone by a carbamate bond.

In one embodiment, the linker arms —R1- and —R'1- are identical.

In one embodiment, the linker arms —R1- and —R'1- are different.

In one embodiment, the linker arms —R1- and —R'1- are chosen from the radicals of formulae II and III

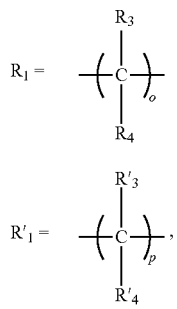

Formula II

Formula III in which:
  o and p, which are identical or different, greater than or equal to 1 and less than or equal to 12, and
  $R_3$ and $R_4$, which are identical or different, are chosen from the group consisting of a hydrogen atom, a saturated or unsaturated, linear, branched or cyclic C1 to C6 alkyl, a benzyl, an alkyl-aryl and optionally containing heteroatoms chosen from the group consisting of O, N and/or S, or functional groups chosen from the group consisting of carboxylic acid, amine, alcohol or thiol,
  $R'_3$ and $R'_4$, which are identical or different, are chosen from the group consisting of a hydrogen atom, a saturated or unsaturated, linear, branched or cyclic C1 to C6 alkyl, a benzyl, an alkyl-aryl and optionally containing heteroatoms chosen from the group consisting of O, N and/or S, or functional groups chosen from the group consisting of carboxylic acid, amine, alcohol or thiol, In one embodiment, the oligosaccharide is characterized in that the radical —R'1- is —CH2-.

In one embodiment, the oligosaccharide is characterized in that the radical —R1- is —CH2-.

In one embodiment, the polysaccharide is characterized in that the radical —R'1- is chosen from the group consisting of the following radicals:

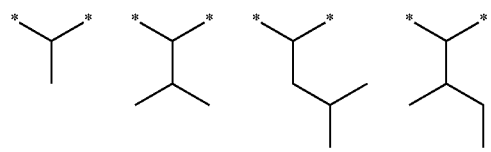

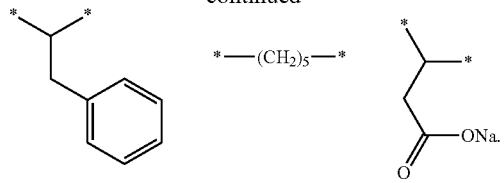

In one embodiment, the polysaccharide is characterized in that the radical —R1- is chosen from the group consisting of the following radicals:

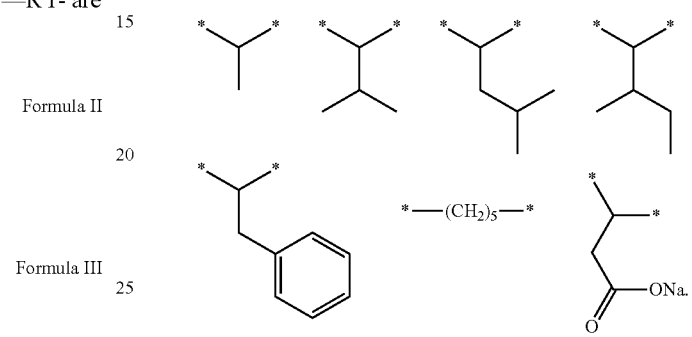

In one embodiment, the oligosaccharide is chosen from oligodextrans.

In one embodiment, the oligodextran has a number-average molar mass of less than 2000 g/mol.

In one embodiment, at least 50% of the oligosaccharide population has a degree of polymerization of less than 10.

The cations are chosen from alkali metal cations such as $Na^+$ or $K^+$.

In one embodiment, the amino acids are chosen from alpha-amino acids.

In one embodiment, the alpha-amino acids are chosen from natural alpha-amino acids.

In one embodiment, the natural alpha-amino acids are chosen from hydrophobic amino acids chosen from the group consisting of tryptophan, leucine, alanine, isoleucine, glycine, phenylalanine, and valine. In one embodiment, the natural alpha-amino acids are chosen from polar amino acids chosen from the group consisting of aspartic acid, glutamic acid, lysine, and serine.

In one embodiment, the natural alpha-amino acids are chosen from polar amino acids chosen from the group comprising aspartic acid, glutamic acid, lysine, serine.

In one embodiment, the oligosaccharide is characterized in that the radical —$R_2$ is a benzyl radical.

In one embodiment, the oligosaccharide is characterized in that the radical —$R_2$ is derived from a hydrophobic alcohol.

In one embodiment, the hydrophobic alcohol is chosen from alcohols consisting of an unsaturated and/or saturated, branched or unbranched alkyl chain comprising from 4 to 18 carbon atoms.

In one embodiment, the hydrophobic alcohol is chosen from alcohols consisting of an unsaturated and/or saturated, branched or unbranched alkyl chain comprising from 6 to 18 carbon atoms.

In one embodiment, the hydrophobic alcohol is chosen from alcohols consisting of an unsaturated and/or saturated, branched or unbranched alkyl chain comprising from 8 to 16 carbon atoms.

In one embodiment, the hydrophobic alcohol is octanol.

In one embodiment, the hydrophobic alcohol is 2-ethylbutanol.

In one embodiment, the fatty alcohol is chosen from meristyl, cetyl, stearyl, cetearyl, butyl, oleyl, lanolin.

In one embodiment, the hydrophobic alcohol is chosen from the group consisting of cholesterol and its derivatives.

In one embodiment, the hydrophobic alcohol is cholesterol.

In one embodiment, the hydrophobic alcohol is chosen from menthol derivatives.

In one embodiment, the hydrophobic alcohol is menthol in its racemic form.

In one embodiment, the hydrophobic alcohol is the D isomer of menthol.

In one embodiment, the hydrophobic alcohol is the L isomer of menthol.

In one embodiment, the hydrophobic alcohol is chosen from tocopherols.

In one embodiment, the tocopherol is alpha-tocopherol.

In one embodiment, the alpha-tocopherol is the racemate of alpha-tocopherol.

In one embodiment, the tocopherol is the D isomer of alpha-tocopherol.

In one embodiment, the tocopherol is the L isomer of alpha-tocopherol.

In one embodiment, the hydrophobic alcohol is chosen from alcohols bearing an aryl group.

In one embodiment, the alcohol bearing an aryl group is chosen from the group consisting of benzyl alcohol and phenethyl alcohol.

In one embodiment, the oligosaccharide is characterized in that the radical —$R_2$ is derived from a hydrophobic acid.

In one embodiment, the hydrophobic acid is chosen from fatty acids.

In one embodiment, the fatty acids are chosen from the group consisting of acids consisting of an unsaturated or saturated, branched or unbranched alkyl chain comprising from 6 to 50 carbon atoms.

In one embodiment, the fatty acids are chosen from the group consisting of linear fatty acids.

In one embodiment, the linear fatty acids are chosen from the group consisting of caproic acid, oenanthic acid, caprylic acid, capric acid, nonanoic acid, decanoic acid, undecanoic acid, dodecanoic acid, palmitic acid, stearic acid, arachidic acid, behenic acid, tricosanoic acid, lignoceric acid, heptacosanoic acid, octacosanoic acid and melissic acid.

In one embodiment, the fatty acids are chosen from the group consisting of unsaturated fatty acids.

In one embodiment, the unsaturated fatty acids are chosen from the group consisting of myristoleic acid, palmitoleic acid, oleic acid, elaidic acid, linoleic acid, alpha-linoleic acid, arachidonic acid, eicosapentaenoic acid, erucic acid and docosahexaenoic acid.

In one embodiment, the fatty acids are chosen from the group consisting of bile acids and their derivatives.

In one embodiment, the bile acids and their derivatives are chosen from the group consisting of cholic acid, dehydrocholic acid, deoxycholic acid and chenodeoxycholic acid.

In one embodiment, $0.1 \leq i \leq 3$
In one embodiment, $0.5 \leq i \leq 2.5$
In one embodiment, $0.7 \leq i \leq 2$
In one embodiment, $0.9 \leq i \leq 1.7$
In one embodiment, $0.01 \leq j \leq 2.9$
In one embodiment, $0.02 \leq j \leq 2$
In one embodiment, $0.03 \leq j \leq 1.2$
In one embodiment, $0.04 \leq j \leq 0.7$ The oligosaccharide according to the invention has an average degree of polymerization of between 2 and 10.

In one embodiment, it has an average degree of polymerization of between 2 and 8.

In another embodiment, it has an average degree of polymerization of between 3 and 6.

The term anionic is understood to mean an oligosaccharide which contains non-functionalized and salifiable carboxyl functional groups.

The expression degree of polymerization DP is understood to mean the average number of repeating units (monomers) per polymer chain. It is calculated by dividing the number-average molar mass by the average mass of the repeated unit.

The expression number-average molar mass ($M_n$) is understood to mean the arithmetic mean of the masses of each of the polymer chains. Thus, for a number $n_i$ of chains i of molar mass $M_i$, $M_n = (\Sigma_i n_i M_i)/(\Sigma_i n_i)$.

The weight-average molar mass ($M_w$) is obtained by $M_w = (\Sigma_i n_i M_i^2)/(\Sigma_i n_i M_i)$, $n_i$ being the number of polymer chains i of molar mass $M_i$.

The polymers may also be characterized by the distribution of chain lengths, also called polydispersity value (Vp), and is equal to $M_w$ divided by $M_n$.

In one embodiment, the invention relates to an oligosaccharide chosen from the group consisting of the following oligosaccharides:

- sodium dextranmethylcarboxylate functionalized by dilauryl aspartate [1DMC(1.03)Asp(OC$_{12}$)$_2$(0.07)]
- sodium dextranmethylcarboxylate functionalized by dilauryl aspartate [1DMC(1.65)Asp(OC$_{12}$)$_2$(0.07)]
- sodium dextranmethylcarboxylate functionalized by dilauryl aspartate [1DMC(1.65)Asp(OC$_{12}$)$_2$(0.15)]
- sodium dextranmethylcarboxylate functionalized by didecyl aspartate [1DMC(1.03)Asp(OC$_{10}$)$_2$(0.05)]
- sodium dextranmethylcarboxylate functionalized by dioctyl aspartate [1DMC(1.03)Asp(OC$_8$)$_2$(0.07)]
- sodium dextranmethylcarboxylate functionalized by β-benzyl aspartate [1DMC(1.65)Asp(OBzl)OH(0.6)]
- sodium dextranmethylcarboxylate functionalized by tryptophan [1DMC(1.65)Trp(1.0)]
- sodium dextranmethylcarboxylate functionalized by octyl phenylalaninate [1DMC(1.03)PheOC$_8$(0.2)]
- sodium dextranmethylcarboxylate functionalized by tryptophan [1DMC(2.1)Trp(1.3)]
- sodium dextranmethylcarboxylate functionalized by phenylalanine [1DMC(1.65)Phe(0.65)]
- sodium dextranmethylcarboxylate functionalized by phenylalanine [1DMC(2.1)Phe(1.0)]
- sodium N-methylcarboxylate dextran carbamate modified by L-phenylalanine [1DUGly(1.65)Phe(0.65)]
- sodium N-methylcarboxylate dextran carbamate modified by tryptophan [1DUGly(1.65)Trp(1.0)]
- sodium dextranmethylcarboxylate functionalized by cholesteryl leucinate [1DMC(1.65)LeuChol(0.05)]
- dextrane modified by sodium carbamate L-phenylalaninate L-aspartate [1DUAspPhe(1.0)].

The invention also relates to the use of the functionalized oligosaccharides according to the invention for the preparation of pharmaceutical compositions.

The invention also relates to a pharmaceutical composition comprising one of the oligosaccharides according to the invention as previously described and at least one active ingredient.

The invention also relates to a pharmaceutical composition characterized in that the active ingredient is chosen from the group consisting of proteins, glycoproteins, peptides and non-peptide therapeutic molecules.

The expression active ingredient is understood to mean a product in the form of a single chemical entity and/or in the form of a combination having a physiological activity. The said active ingredient may be exogenous, that is to say that it is provided by the composition according to the invention. It may also be endogenous, for example growth factors which will be secreted into a wound during the first phase of wound healing and which may be kept on the said wound by the composition according to the invention.

Depending on the pathologies targeted, it is intended for local and/or systemic treatment.

In the case of local and systemic releases, the modes of administration envisaged are by the intravenous, subcutaneous, intradermal, transdermal, intramuscular, oral, nasal, vaginal, ocular, buccal and pulmonary routes, and the like.

The pharmaceutical compositions according to the invention are either in liquid form, in aqueous solution, or in the form of a powder, an implant or a film. They additionally contain conventional pharmaceutical excipients well known to persons skilled in the art.

According to the pathologies and the modes of administration, the pharmaceutical compositions may additionally advantageously contain excipients which make it possible to formulate them in the form of a gel, a sponge, an injectable solution, an oral solution, an oral lyophilisate, and the like.

The invention also relates to a pharmaceutical composition, characterized in that it is administrable in the form of a stent, a film or a "coating" of implantable biomaterials, an implant.

EXAMPLES

TABLE 1

| Oligosaccharide | Substituent —$R_1$—COONa (m = 0) | Substituent —$R_1$—[[AA]—[$R_2$]$_n$]$_m$ |
|---|---|---|
| OS1 | | |
| OS2 | | |
| OS3 | | |
| OS4 | | |
| OS5 | | |

TABLE 1-continued

| | Oligosaccharides | |
|---|---|---|
| Oligo-saccharide | Substituent —R$_1$—COONa (m = 0) | Substituent —R$_1$—[[AA]—[R$_2$]$_n$]$_m$ |
| OS6 | -O-CH$_2$-C(=O)-ONa | glycolyl-Asp with both carboxylic acids esterified as -O-(CH$_2$)$_7$-CH$_3$ (dioctyl aspartate) |
| OS7 | -O-CH$_2$-C(=O)-ONa | glycolyl-Asp α-benzyl ester, free β-COOH |
| OS8 | -O-CH$_2$-C(=O)-ONa | glycolyl-Trp-ONa |
| OS9 | -O-CH$_2$-C(=O)-ONa | glycolyl-Trp-ONa |
| OS10 | -O-CH$_2$-C(=O)-ONa | glycolyl-Phe-ONa |
| OS11 | -O-CH$_2$-C(=O)-ONa | glycolyl-Phe-ONa |

TABLE 1-continued

Oligosaccharides

| Oligo-saccharide | Substituent —$R_1$—COONa (m = 0) | Substituent —$R_1$—[[AA]—[$R_2$]$_n$]$_m$ |
|---|---|---|
| OS12 | 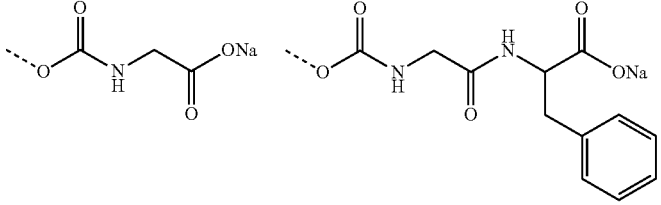 | |
| OS13 | 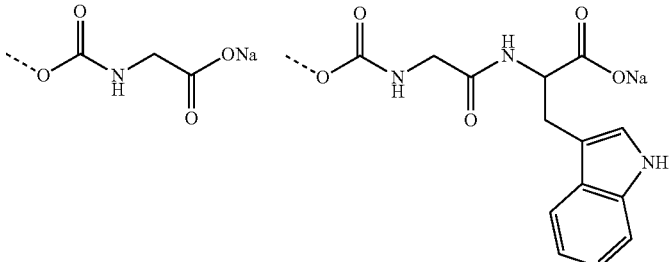 | |
| OS14 | 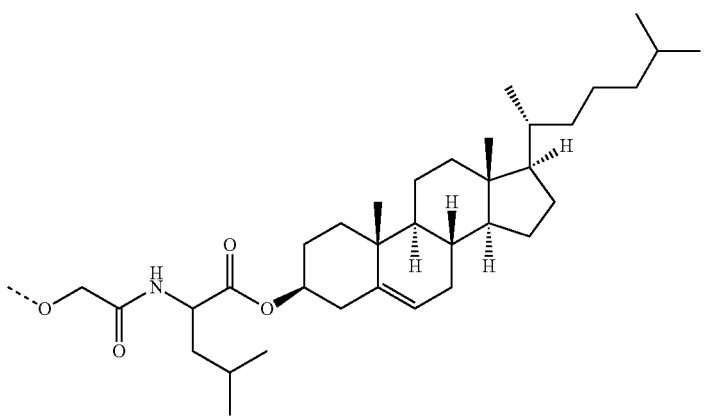 | |
| OS15 | 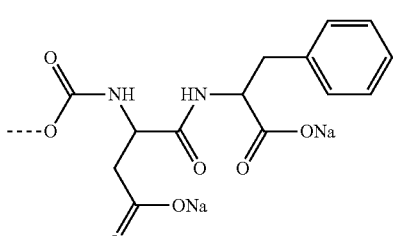 | |

Oligosaccharide 1: Sodium Dextranmethylcarboxylate Functionalized by Octyl Phenylalaninate [1DMC(1.03)PheOC$_8$(0.2)]

Octyl phenylalaninate, salt of para-toluenesulphonic acid, is prepared from octanol and phenylalanine according to the process described in U.S. Pat. No. 4,826,818 (Kenji M., et al.).

8 g (148 mmol of hydroxyl functional groups) of dextran having a weight-average molar mass of 1 kg/mol (Pharmacosmos, degree of polymerization of 3.9), are dissolved in water (420 g/l). To this solution are added 15 ml of 10 N NaOH (48 mmol). The mixture is heated to 35° C., and 23 g of sodium chloroacetate (198 mmol) are added. The mixture is gradually heated to a temperature of 60° C. and maintained at this temperature for 100 additional minutes. The mixture is diluted with water, neutralized with acetic acid and then purified by ultrafiltration on PES membrane of 1 kDa against water. The oligosaccharide concentration of the final solution is determined by the dry extract, and then an acid/base assay in a 50/50 (V/V) water/acetone mixture is carried out in order to determine the degree of substitution with methyl carboxylate.

According to the dry extract: [oligosaccharide]=31.5 mg/g.

According to the acid/base assay, the degree of substitution with methyl carboxylate is 1.03 per glucoside unit. This sodium dextranmethylcarboxylate is freeze-dried for 18 hours.

The sodium dextranmethylcarboxylate solution is acidified on a Purolite (anionic) resin in order to obtain dextranmethylcarboxylic acid which is then freeze-dried for 18 hours.

10 g of dextranmethylcarboxylic acid (46 mmol of methylcarboxylic acid functional groups) are solubilized in DMF (23 g/l) and then cooled to 0° C. A mixture of octyl phenylalaninate, para-toluenesulphonic acid salt (4.0 g; 9 mmol) in DMF is prepared (100 g/l). 0.9 g of triethylamine (9 mmol) is added to the mixture. Once the oligosaccharide solution is at 0° C., a solution of NMM (5.2 g, 51 mmol) and of EtOCOCl (5.6 g; 51 mmol) is added. After 10 minutes, the octyl phenylalaninate solution is added and the mixture is stirred at 10° C. The mixture is then heated to 50° C. 70 ml of an aqueous imidazole solution (150 g/l) and 120 ml of water are added. The solution thus obtained is purified by ultrafiltration on a PES membrane of 1 kDa against 0.9% NaCl, 0.01N NaOH, 0.9% NaCl and water. The oligosaccharide concentration of the final solution is determined by the dry extract. A sample of solution is freeze-dried and analysed by $^1$H NMR in $D_2O$ in order to determine the degree of substitution with methyl carboxylates grafted by the octyl phenylalaninate.

According to the dry extract: [Oligosaccharide 1]=11.1 mg/g.

According to $^1$H NMR: the degree of substitution with methyl carboxylates grafted by the octyl phenylalaninate is 0.2.

Oligosaccharide 2: Sodium Dextranmethylcarboxylate Functionalized by Dilauryl Aspartate [1DMC(1.03)Asp(OC$_{12}$)$_2$(0.07)]

Dilauryl aspartate, salt of para-toluenesulphonic acid, is prepared from dodecanol and aspartic acid according to the process described in U.S. Pat. No. 4,826,818 (Kenji M., et al.).

10 g of dextranmethylcarboxylic acid characterized by a degree of substitution with methyl carboxylate of 1.03 per glucoside unit are synthesized from a dextran having a weight-average molar mass of 1 kg/mol (Pharmacosmos, degree of polymerization of 3.9), according to a process similar to the one described for oligosaccharide 1, and then freeze-dried.

Using a process similar to the one used for the preparation of oligosaccharide 1, a sodium methyl carboxylate dextran functionalized by dilauryl aspartate is obtained.

According to the dry extract: [Oligosaccharide 2]=12.3 mg/g.

According to $^1$H NMR: the degree of substitution with methyl carboxylates functionalized by dilauryl aspartate is 0.07.

Oligosaccharide 3: Sodium Dextranmethylcarboxylate Functionalized by Dilauryl Aspartate [1DMC(1.65)Asp(OC$_{12}$)$_2$(0.07)]

10 g of sodium dextranmethylcarboxylate characterized by a degree of substitution with methyl carboxylate of 1.03 per glucoside unit are synthesized from a dextran having a weight-average molar mass of 1 kg/mol (Pharmacosmos, degree of polymerization of 3.9), according to a process similar to the one described for the oligosaccharide 1, and then freeze-dried.

8 g (64 mmol of hydroxyl functional groups) of sodium dextranmethylcarboxylate characterized by a degree of substitution with methyl carboxylate of 1.03 per glucoside unit are solubilized in water (1000 g/l). 6 ml of 10 N NaOH (64 mmol) are added. The mixture is heated to 35° C. and 7.6 g of sodium chloroacetate (65 mmol) are added. The mixture is gradually heated to a temperature of 60° C. and is kept at this temperature for an additional 100 minutes. The mixture is diluted with water, neutralized with acetic acid and then purified by ultrafiltration on a PES membrane of 1 kDa against water. The oligosaccharide concentration of the final solution is determined by the dry extract, and then an acid/base assay in a 50/50 (V/V) water/acetone mixture is carried out in order to determine the degree of substitution with methyl carboxylate.

According to the dry extract: [oligosaccharide]=45.8 mg/g.

According to the acid/base assay, the degree of substitution with methyl carboxylate is 1.65 per glucoside unit.

The sodium dextranmethylcarboxylate solution is passed over a Purolite (anionic) resin in order to obtain dextranmethylcarboxylic acid which is then freeze-dried for 18 hours.

Oligosaccharide 3 is a sodium dextranmethylcarboxylate functionalized by dilauryl aspartate prepared according to a process similar to the one described for Oligosaccharide 2.

Dry extract: [Oligosaccharide 3]=17.5 mg/g.

According to $^1$H NMR: the degree of substitution with methyl carboxylates functionalized by dilauryl aspartate is 0.07.

Oligosaccharide 4: Sodium Dextranmethylcarboxylate Functionalized by Dilauryl Aspartate [1DMC(1.65)Asp(OC$_{12}$)$_2$(0.15)]

10 g of dextranmethylcarboxylic acid characterized by a degree of substitution with methyl carboxylate of 1.65 per glucoside unit are synthesized from a dextran having a weight-average molar mass of 1 kg/mol (Pharmacosmos, degree of polymerization of 3.9) according to a process similar to the one described for Oligosaccharide 3, and then freeze-dried.

Oligosaccharide 4 is a sodium dextranmethylcarboxylate functionalized by dilauryl aspartate, prepared according to a process similar to the one described for Oligosaccharide 2.

According to the dry extract: [Oligosaccharide 4]=16.7 mg/g.

According to $^1$H NMR: the degree of substitution with methyl carboxylates functionalized by dilauryl aspartate is 0.15.

Oligosaccharide 5: Sodium Dextranmethylcarboxylate Functionalized by Didecyl Aspartate [1DMC(1.03)Asp(OC$_{10}$)$_2$(0.05)]

Didecyl aspartate, salt of para-toluenesulphonic acid, is prepared from decanol and aspartic acid according to the process described in U.S. Pat. No. 4,826,818 (Kenji M., et al.).

10 g of dextranmethylcarboxylic acid characterized by a degree of substitution with methyl carboxylate of 1.03 per glucoside unit are synthesized from a dextran having a weight-average molar mass of 1 kg/mol (Pharmacosmos, degree of polymerization of 3.9) according to a process similar to the one described for Oligosaccharide 1, and then freeze-dried.

Oligosaccharide 5 is a sodium dextranmethylcarboxylate functionalized by didecyl aspartate, prepared according to a process similar to the one described for Oligosaccharide 2.

According to the dry extract: [Oligosaccharide 5]=19.4 mg/g.

According to $^1$H NMR: the degree of substitution with methyl carboxylates functionalized by didecyl aspartate is 0.05.

Oligosaccharide 6: Sodium Dextranmethylcarboxylate Functionalized by Dioctyl Aspartate [1DMC(1.03)Asp(OC$_8$)$_2$(0.07)]

Dioctyl aspartate, salt of para-toluenesulphonic acid, is prepared from octanol and aspartic acid according to the process described in U.S. Pat. No. 4,826,818 (Kenji M., et al.).

10 g of dextranmethylcarboxylic acid characterized by a degree of substitution with methyl carboxylate of 1.03 per glucoside unit are synthesized from a dextran having a weight-average molar mass of 1 kg/mol (Pharmacosmos, degree of polymerization of 3.9) according to a process similar to the one described for Oligosaccharide 1, and then freeze-dried.

Oligosaccharide 6 is a sodium dextranmethylcarboxylate functionalized by dioctyl aspartate, prepared according to a process similar to the one described for Oligosaccharide 2.

According to the dry extract: [Oligosaccharide 6]=9.8 mg/g.

According to $^1$H NMR: the degree of substitution with methyl carboxylates functionalized by dioctyl aspartate is 0.07.

Oligosaccharide 7: Sodium Dextranmethylcarboxylate Functionalized by 3-benzyl Aspartate [1DMC(1.65)Asp(OBzl)OH(0.6)]

10 g of dextranmethylcarboxylic acid characterized by a degree of substitution with methyl carboxylate of 1.65 per glucoside unit are synthesized from a dextran having a weight-average molar mass of 1 kg/mol (Pharmacosmos, degree of polymerization of 3.9) according to a process similar to the one described for Oligosaccharide 3, and then freeze-dried.

Oligosaccharide 7 is a sodium dextranmethylcarboxylate functionalized by β-benzyl aspartate, prepared according to a process similar to the one described for Oligosaccharide 2 using aspartic acid of β-benzyl (Bachem).

According to the dry extract: [Oligosaccharide 7]=26.0 mg/g.

According to $^1$H NMR: the degree of substitution with methyl carboxylates functionalized by β-benzyl aspartate is 0.6.

Oligosaccharide 8: Sodium Dextranmethylcarboxylate Functionalized by Tryptophan [1DMC(1.65)Trp(1.0)]

10 g of dextranmethylcarboxylic acid characterized by a degree of substitution with methyl carboxylate of 1.65 per glucoside unit are synthesized from a dextran having a weight-average molar mass of 1 kg/mol (Pharmacosmos, degree of polymerization of 3.9) according to a process similar to the one described for Oligosaccharide 3, and then freeze-dried.

10 g of dextranmethylcarboxylic acid (64 mmol of methylcarboxylic acid functional groups) are solubilized in DMF (22 g/l) and then cooled to 0° C. Once the oligosaccharide solution is at 0° C., a solution of NMM (7.1 g; 70 mmol) and EtOCOCl (7.6 g; 70 mmol) is added. After 10 minutes, 11.9 g of tryptophan (Ajinomoto) (58 mmol) are added and the mixture is stirred at 10° C. 26 ml of an aqueous solution of imidazole (340 g/l) are added. The mixture is then heated to 30° C. When the temperature reaches 20° C., 70 ml of water are added. When the temperature reaches 30° C., the mixture is taken out of the reactor and the solution obtained is purified by ultrafiltration on a PES membrane of 1 kDa against 6 volumes of 0.9% NaCl, 2 volumes of 0.01N NaOH, 4 volumes of 0.9% NaCl and 3 volumes of water. The oligosaccharide concentration of the final solution is determined by the dry extract. A sample of solution is freeze-dried and analysed by $^1$H NMR in $D_2O$ in order to determine the molar fraction of methyl carboxylates grafted by the tryptophan.

According to the dry extract: [Oligosaccharide 8]=47.1 mg/g.

According to $^1$H NMR: the degree of substitution with methyl carboxylates functionalized by tryptophan is 1.

Oligosaccharide 9: Sodium Dextranmethylcarboxylate Functionalized by Tryptophan [1DMC(2.1)Trp(1.3)]

10 g of sodium dextranmethylcarboxylate characterized by a degree of substitution with methyl carboxylate of 1.65 per glucoside unit are synthesized from a dextrane having a weight-average molar mass of 1 kg/mol (Pharmacosmos, degree of polymerization of 3.9) according to a process similar to the one described for Oligosaccharide 2, and then freeze-dried.

8 g (37 mmol of hydroxyl functional groups) of dextranmethylcarboxylate characterized by a degree of substitution with methyl carboxylate of 1.65 per glucoside unit are solubilized in water (430 g/l). The solution is heated to 65° C. and 11.1 g of sodium chloroacetate are added. The mixture at 65° C. is stirred for 30 minutes. 14 ml of NaOH 10N (136 mmol) are added dropwise. Next, the mixture is stirred at 65° C. The mixture is diluted with water, neutralized with acetic acid and then purified by ultrafiltration on a PES membrane of 1 kDa against water. The oligosaccharide concentration of the final solution is determined by the dry extract, and then an acid/base assay in a 50/50 (V/V) water/acetone mixture is carried out in order to determine the degree of substitution with methyl carboxylate.

According to the dry extract: [Oligosaccharide]=25.8 mg/g.

According to the acid/base assay, the degree of substitution with methyl carboxylate is 2.1 per glucoside unit.

The sodium dextranmethylcarboxylate solution is passed over a Purolite (anionic) resin in order to obtain the dextranmethylcarboxylic acid which is then freeze-dried for 18 hours.

Oligosaccharide 9 is a sodium dextranmethylcarboxylate functionalized by tryptophan, prepared according to a process similar to the one described for Oligosaccharide 8.

According to the dry extract: [Oligosaccharide 9]=31.1 mg/g.

According to $^1$H NMR: the degree of substitution with methyl carboxylates functionalized by tryptophan is 1.3.

Oligosaccharide 10: Sodium Dextranmethylcarboxylate Functionalized by Phenylalanine [1DMC(1.65)Phe(0.65)]

10 g of dextranmethylcarboxylic acid characterized by a degree of substitution with methyl carboxylate of 1.65 per glucoside unit are synthesized from a dextran having a weight-average molar mass of 1 kg/mol (Pharmacosmos, degree of polymerization of 3.9) according to a process similar to the one described for Oligosaccharide 3, and then freeze-dried.

10 g of dextranmethylcarboxylic acid (64 mmol of methylcarboxylic acid functional groups) are solubilized in DMF (58 g/l) and then cooled to 0° C. A mixture of ethyl phenylalaninate, hydrochloride salt (6.2 g; 27 mmol) in DMF is prepared (100 g/l). 2.7 g of triethylamine (27 mmol) are added to this mixture. Once the oligosaccharide solution is at 0° C., a solution of NMM (6.5 g, 64 mmol) and EtOCOCl (6.9 g; 64 mmol) is added. After 10 minutes, the ethyl phenylalaninate solution is added and the mixture is stirred at 10° C. An aqueous solution of imidazole (340 g/l) is added. The solution is then heated to 30° C. 70 ml of water are added and the solution obtained is purified by ultrafiltration on a PES membrane of 1 kDa against 7 volumes of 0.1N NaOH, 7 volumes of 0.9% NaCl and 3 volumes of water. The oligosaccharide concentration of the final solution is determined by the dry extract. A sample of solution is freeze-dried and analysed by $^1$H NMR in $D_2O$ in order to determine the molar fraction of methyl carboxylates grafted by the phenylalanine.

According to the dry extract: [Oligosaccharide 10]=24.2 mg/g.

According to $^1$H NMR: the degree of substitution with methyl carboxylates functionalized by phenylalanine is 0.65.

Oligosaccharide 11: Sodium Dextranmethylcarboxylate Functionalized by Phenylalanine [1DMC(2.1)Phe(1.0)]

10 g of dextranmethylcarboxylic acid characterized by a degree of substitution with methyl carboxylate of 2.1 per glucoside unit are synthesized from a dextran having a weight-average molar mass of 1 kg/mol (Pharmacosmos, degree of polymerization of 3.9), according to a process similar to the one described for Oligosaccharide 9, and then freeze-dried.

Oligosaccharide 11 is a sodium dextranmethylcarboxylate functionalized by phenylalanine, prepared according to a process similar to the one described for Oligosaccharide 10.

According to the dry extract: [Oligosaccharide 11]=31.8 mg/g.

According to $^1$H NMR: the degree of substitution with methyl carboxylates functionalized by phenylalanine is 1.

Oligosaccharide 12: Sodium N-methylcarboxylate Dextran Carbamate Modified by L-phenylalanine [1DUGly(1.65)Phe(0.65)]

8 g (that is 148 mmol of hydroxyl functional groups) of dextran having a weight-average molar mass of about 1 kg/mol (Pharmacosmos, degree of polymerization of 3.9) are solubilized in a DMF/DMSO mixture, in the presence of NaBH$_4$ (0.5 g; 13 mmol). After stirring for 30 minutes, DABCO (1,4-diazabicyclo[2.2.2]octane, 2.2 g; 20 mmol) and 9 ml of toluene are added to the mixture which is heated to 120° C. with stirring and heteroazeotropically distilled. After the reaction mixture has returned to 80° C., 19.1 g (148 mmol) of ethyl isocyanatoacetate are gradually introduced. After 1.5 hours of reaction, the medium is diluted in water and purified by diafiltration on a PES membrane of 1 kDa against 0.1N NaOH, 0.9% NaCl and water. The final solution is assayed by the dry extract in order to determine the oligosaccharide concentration, and then assayed by acid/base assay in 50/50 (V/V) water/acetone in order to determine the degree of substitution with carboxylate charges.

According to the dry extract: [polymer]=25.0 mg/g.

According to the acid/base assay, The degree of substitution of the hydroxyl functional groups with N-methylcarboxylate carbamate functional groups is 1.65 per saccharide unit.

The solution of sodium N-methylcarboxylate dextran carbamate is acidified on a Purolite (anionic) resin in order to obtain dextran-N-methylcarboxylic acid which is then freeze-dried for 18 hours.

Oligosaccharide 12 is a sodium N-methylcarboxylate dextran carbamate functionalized by phenylalanine, prepared according to a process similar to the one described for Oligosaccharide 10.

According to the dry extract: [Oligosaccharide 12]=23.8 mg/g.

According to $^1$H NMR: the degree of substitution with N-methyl carboxylates functionalized by phenylalanine is 0.65.

Oligosaccharide 13: Sodium N-methylcarboxylate Dextran Carbamate Modified by Tryptophan [1DUGly(1.65)Trp(1.0)]

10 g of dextran-N-methylcarboxylic acid characterized by a degree of substitution with N-methylcarboxylate of 1.65 per glucoside unit are synthesized from a dextran having a weight-average molar mass of 1 kg/mol (Pharmacosmos, degree of polymerization of 3.9), according to a process similar to the one described for Oligosaccharide 12, and then freeze-dried.

Oligosaccharide 13 is a sodium N-methylcarboxylate dextran carbamate functionalized by tryptophan, prepared according to a process similar to the one described for Oligosaccharide 9.

According to the dry extract: [Oligosaccharide 13]=37.1 mg/g.

According to $^1$H NMR: the degree of substitution with N-methylcarboxylates functionalized by tryptophan is 1.

Oligosaccharide 14: Sodium Dextranmethylcarboxylate Functionalized by Cholesteryl Leucinate [1DMC(1.65)LeuChol(0.05)]

10 g of dextranmethylcarboxylic acid characterized by a degree of substitution with methyl carboxylate of 1.65 per glucoside unit are synthesized from a dextrane having a weight-average molar mass of 1 kg/mol (Pharmacosmos, degree of polymerization of 3.9), according to a process similar to the one described for Oligosaccharide 3, and then freeze-dried.

Cholesteryl leucinate, salt of para-toluenesulphonic acid, is prepared from cholesterol and leucine according to the process described in U.S. Pat. No. 4,826,818 (Kenji M., et al.).

Oligosaccharide 14 is a sodium dextranmethylcarboxylate functionalized by cholesteryl leucinate, prepared according to a process similar to the one described for Oligosaccharide 1.

According to the dry extract: [Oligosaccharide 14]=13.7 mg/g.

According to $^1$H NMR: the degree of substitution with methyl carboxylates functionalized by cholesteryl leucinate is 0.05.

Oligosaccharide 15: Dextrane Modified by Sodium Carbamate L-phenylalaninate L-aspartate [1DUAspPhe(1.0)]

Ethyl L-phenylalaninate β-benzyl L-aspartate hydrochloride is synthesized according to a peptide-coupling method described in the publication (Carpino et al. J. Org. Chem. 1995, 60, 3561) from 2-[(tert-butoxycarbonyl)amino]-4-benzyloxy-4-oxobutanoic acid (Boc-Asp(OBzl)-OH, available from Bachem) and ethyl L-phenylalaninate hydrochloride HCl-PheOEt followed by deprotection of the tert-butoxycarbonyl (Boc) group in hydrochloric acid at 0° C.

Isocyanate of the dipeptide ethyl L-phenylalaninate β-benzyl L-aspartate is obtained according to the process described in the publication (Tsai, J. H. et al. Organic Synthesis 2004, 10, 544-545) from ethyl L-phenylalaninate β-benzyle L-aspartate hydrochloride and triphosgene (Sigma).

Grafting of the isocyanate of the dipeptide ethyl L-phenylalaninate β-benzyle L-aspartate onto the dextran is carried out according to the process described in the publication (Arranz, F. et al. Makromol. Chemie 1987, 188, 2831-2838). 4 g (that is 0.07 mol of hydroxyl functional groups) of dextran having a weight-average molar mass of about 1 kg/mol (Pharmacosmos) are solubilized in a DMF/DMSO mixture, in the presence of DABCO (1,4-diazabicyclo[2.2.2]octane). Toluene is added to the mixture and the medium is dehydrated by heteroazeotropic distillation. At 80° C., 15.8 g (0.04 mol) of isocyanate of the dipeptide ethyl L-phenylalaninate β-benzyle L-aspartate are gradually introduced. After 12 hours of reaction the medium is diluted in water and purified by diafiltration on a PES membrane of 5 kD against 0.1N NaOH, 0.9% NaCl and water. The final solution is assayed by the dry extract in order to determine the polymer concentration, assayed by acid/base assay in 50/50 (V/V) water/acetone and then analysed by $^1$H NMR in order to determine the degree of functionalization of the hydroxyls with sodium L-phenylalaninate L-aspartate carba mate.

According to the dry extract: [Oligosaccharide 15]=13.7 mg/g.

According to the acid/base assay and $^1$H NMR: the degree of substitution with sodium L-phenylalaninate L-aspartate carbamate is 1.0.

Example 16

Study of the comparative removals of oligosaccharide 10 1DMC(1.65)Phe(0.65) and of its analogue 10DMC(1.1)Phe(0.45) through a membrane with a 30 kDa cut-off.

10DMC(1.1)Phe(0.45) is synthesized according to the same process as oligosaccharide 10 from dextran having a weight-average molar mass of 10 kg/mol (Pharmacosmos, degree of polymerization of 19).

The literature shows, based on dextran, a correlation between the molecular weight and the renal elimination of macromolecules (Caulfield, J. et al. The Journal of Cell biology 1974, 63, 883-903; Chang R. L. S. Kidney International 1975, 8, 212-218). These results show that macromolecules having a molecular weight greater than 30 kDa are difficult to remove by the kidney.

A solution of 250 ml of oligosaccharide 10 at 20 g/l is ultrafiltered on a PES membrane of 30 kDa against 20 volumes of water. The oligosaccharide concentration of the final solution is determined by the dry extract and indicates a recovery of less than 10%.

[Oligosaccharide 10]<2 mg/g.

A solution of 250 ml of 10DMC(1.1)Phe(0.65) at 20 g/l is ultrafiltered on a PES membrane of 30 kDa against 20 volumes of water. The polymer concentration of the final solution is determined by the dry extract.

[10DMC(1.1)Phe(0.45)]>12 mg/g. The polymer was recovered after ultrafiltration with a yield greater than 60%.

These results confirm that these oligosaccharides may be removed by filtration a lot more efficiently than polymers of higher molecular mass.

Example 17

Solubilization of BMP-7 at Neutral pH at a Polymer/BMP-7 Mass Ratio of 10

A test of solubilization of Bone Morphogenetic Protein 7 (BMP-7) was developed in order to demonstrate the solubilizing power of various polymers at physiological pH. BMP-7 is soluble at acidic pH and has a very low solubility limit at physiological pH of the order of a few micrograms/ml.

The oligosaccharides described in this application are used in this test. The test consists in using a solution of BMP-7 at acidic pH, for example a 10 mM lactate buffer at pH 3. BMP-7 is at an initial concentration of 2.47 mg/ml. 2.02 ml of this BMP-7 solution are mixed with 2.7 ml of a polymer solution at 18.5 mg/ml containing 18 mM of phosphate buffer at pH 7.4. After mixing, the final pH is adjusted to physiological pH by adding a mixture of 1N sodium hydroxide and water in order to obtain a final volume of formulation of 5 ml. The formulations are analysed by visual observation, turbidity and dynamic diffusion of light in order to detect the presence of aggregates.

The results for the various solutions are assembled in the following table.

| Polymer | [Polymer] mg/ml | [BMP-7] mg/ml | Solubility | pH |
|---|---|---|---|---|
| None | | 1 | No | 7.4 |
| Oligosaccharide 2 | 10 | 1 | Yes | 7.4 |
| Oligosaccharide 3 | 10 | 1 | Yes | 7.4 |

By way of comparison, a polymer having a weight-average molar mass of 10 kDa functionalized by the same substituents, methyl carboxylates and dilauryl aspartate with similar degrees of functionalization leads to the same result.

The oligosaccharides according to the invention therefore make it possible to form complexes with a protein despite a greatly reduced number of saccharide units.

The invention claimed is:

1. Oligodextran, chosen from dextrans whose average degree of polymerization is between 2 and 8, modified by
    at least one substituent of general formula:

$R_1$-[AA]$_m$;

the substituents being identical or different when there are at least two substituents, in which:
        the radical -[AA]- denotes a phenylalanine residue attached to the dextran backbone by means of a linker arm —$R_1$—,
        the linker arm —$R_1$— is a C1 to C15 carbon chain optionally substituted and/or containing at least one heteroatom and optionally a carboxylic acid functional group; it forms with the phenylalanine residue [AA] an amide bond and is directly attached to the oligodextran backbone by an ester, carbamate or ether type bond,
        m being 1 or 2, and
        the degree of substitution j, with —$R_1$-[AA]$_m$, being from 0.01 to 2.9, and
    optionally
    one or more substituents of the same general formula, in which m=0,
        $R_1$ is a C1 to C15 carbon chain, optionally substituted and/or containing at least one heteroatom and at least one carboxylic acid functional group,
        the degree of substitution i, with —$R_1$, being from 0.1 to 2.99,
        i+j≤3, and
    the free salifiable functional groups are in a form of cation salts.

2. The oligodextran according to claim 1, wherein the oligodextran has a number-average molar mass of less than 2000 g/mol.

3. The oligodextran according to claim 1, wherein the oligodextran is chosen from the group consisting of the following oligosaccharides:
    sodium dextranmethylcarboxylate functionalized by phenylalanine [1DMC(1.65)Phe(0.65)];
    sodium dextranmethylcarboxylate functionalized by phenylalanine [1DMC(2.1)Phe(1.0)]; and
    sodium N-methylcarboxylate dextran carbamate modified by L-phenylalanine[1DUGly(1.65)Phe(0.65)].

4. Pharmaceutical composition comprising the oligodextran according to claim 1 and an active ingredient chosen from the group consisting of proteins, glycoproteins, peptides and non-peptide therapeutic molecules.

* * * * *

UNITED STATES PATENT AND TRADEMARK OFFICE
CERTIFICATE OF CORRECTION

| | | |
|---|---|---|
| PATENT NO. | : 9,018,190 B2 | Page 1 of 1 |
| APPLICATION NO. | : 13/468849 | |
| DATED | : April 28, 2015 | |
| INVENTOR(S) | : Charvet et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 123 days.

Signed and Sealed this
Nineteenth Day of April, 2016

Michelle K. Lee
*Director of the United States Patent and Trademark Office*